United States Patent [19]

Plaza

[11] Patent Number: 4,738,251
[45] Date of Patent: Apr. 19, 1988

[54] CORRECTING DEVICE FOR SPINE PATHOLOGY

[75] Inventor: Carlos L. Plaza, Montevideo, Uruguay

[73] Assignee: Codespi, Corporation, Miami, Fla.

[21] Appl. No.: 17,050

[22] Filed: Feb. 20, 1987

[51] Int. Cl.[4] ............................................. A61B 17/56
[52] U.S. Cl. ...................................................... 128/69
[58] Field of Search .......................................... 128/69

[56] References Cited

U.S. PATENT DOCUMENTS

| 4,505,268 | 3/1985 | Sgandurra | 128/69 |
| 4,573,454 | 3/1986 | Hoffman | 128/69 |
| 4,604,995 | 8/1986 | Stephens et al. | 128/69 |

FOREIGN PATENT DOCUMENTS

| 0644472 | 1/1979 | U.S.S.R. | 128/69 |
| 1063404 | 12/1983 | U.S.S.R. | 128/69 |

OTHER PUBLICATIONS

H. S. Struttman, Inc., Fishbein's Illustrated Medical & Health Encyclopedia, vol. #20, 1981, 2743, 2744.
H. S. Struttman, Inc., Fishbein's Illustrated Medical & Health Encyclopedia, vol. #17, 1981, 2225–2228.
Scoliosis and Kyphosis Article, pp. 351, 352 and 354.
Edwardo R. Luque, M.D., Segmental Spinal Instrumentation, pp. 1–10.
Paul R. Harrington, M.D.; Treatment of Scoliosis Correction and Internal Fixation by Spine Instrumentation; vol. 44-A, No. 4, Jun. 1962, pp. 591–610.

Primary Examiner—Edgar S. Burr
Assistant Examiner—Huong Q. Pham
Attorney, Agent, or Firm—Jesus Sanchelima

[57] ABSTRACT

A device for surgically correcting and stabilizing spine deformations in scoliosis patients. Two rigid elongated members, parallel to each other, are kept in a spaced apart relationship by two curved rigid members mounted on their ends. Several hook members are provided to cooperate with wire that is tied around the vertebrae adjacent to the ends of the elongated members.

5 Claims, 1 Drawing Sheet

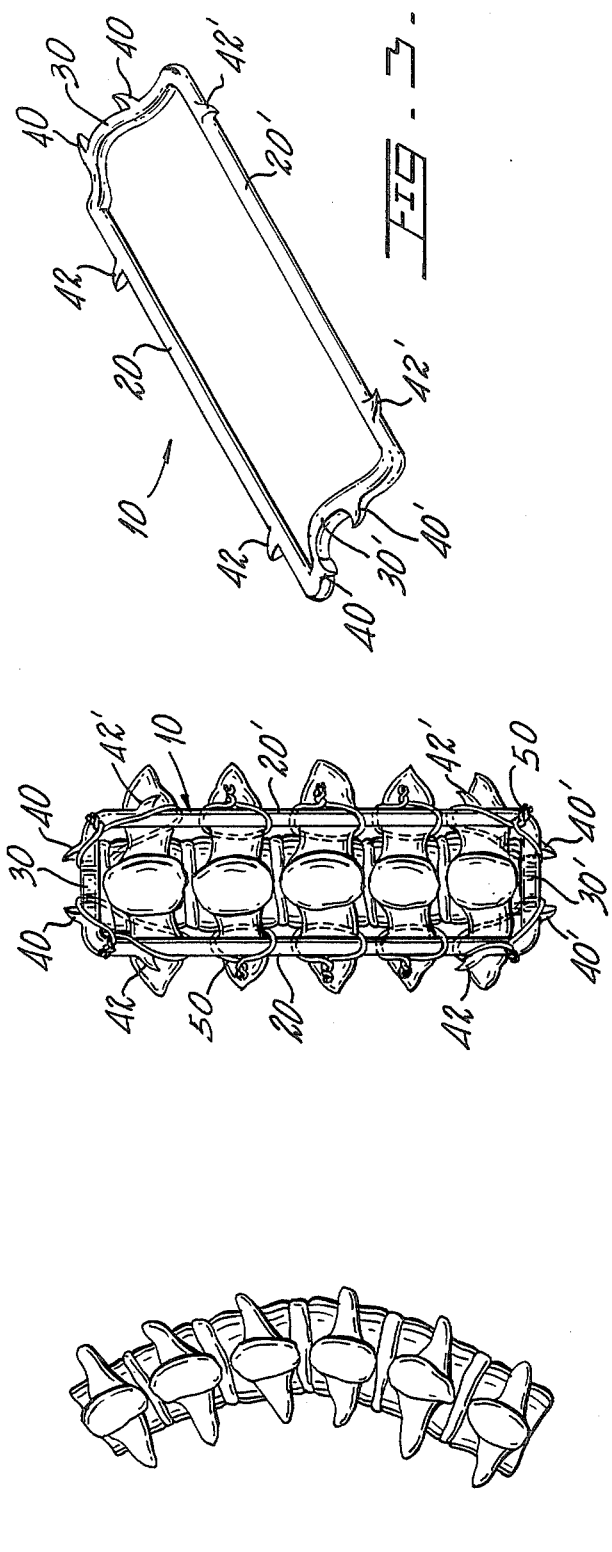

CORRECTING DEVICE FOR SPINE PATHOLOGY

BACKGROUND OF THE INVENTION

1. Field of the Invention

The present invention relates to a device for surgically correcting and stabilizing spine deformations, and more particularly, to such a device that effectively provides support to the vertebrae affected.

2. Description of the Related Art

Several devices have been used in the past to surgically correct severe spine deformations, in particular scoliosis, kyphosis, lordosis, fractures and dislocations of the vertebrae. One of them is the Harrington bar which is basically an adjustable bar that is secured to the ends of the spinal section affected that is intended to be distended in order to approach the normal shape. One problem with Harrington's device is that it provides little correction. The correction is improved when wires are used to attach the bar to the user's vertebrae.

Another device used is the one known as the Luque device which consists of two bars (L-shape) and wires to attach the bars to the vertebrae. However, it is difficult to maintain the bars parallel to each other with Luque's device.

SUMMARY OF THE INVENTION

It is one of the main objects of the present invention to provide a device to surgically correct and stabilize severe deformations of the spine, stabilize fractures of vertebrae and reduce their dislocation.

It is another object of this present invention to provide a device that can be used on any section of vertebrae of the spine.

It is still another object of this invention to provide a device that is capable of rotating the vertebrae back to the normal position or at least approach it.

It is yet another object of the present invention to provide such a device that is inexpensive to manufacture and maintain while retaining its effectiveness.

Further objects of the invention will be brought out in the following part of the specification, wherein detailed description is for the purpose of fully disclosing the invention without placing limitations thereon.

BRIEF DESCRIPTION OF THE DRAWINGS

With the above and other related objects in view, the invention consists in the details of construction and combination of parts as will be more fully understood from the following description, when read in conjunction with the accompanying drawings in which:

FIG. 1 represents a section of a deformed spine.

FIG. 2 shows the section of FIG. 1 with the correcting device mounted thereon.

FIG. 3 illustrates a view in perspective of the device.

DETAILED DESCRIPTION OF THE PREFERRED EMBODIMENT

Referring now to FIGS. 1 and 2, it can be observed that correcting device 10 is used to bring a deformed spine to normal alignment.

Basically, correcting device 10 includes two elongated rigid members 20 and 20', parallel to each other and spaced apart by two curved rigid members 30 and 30' that are rigidly mounted on the ends of members 20 and 20'. Member 20 and 20' include, each, two ends where curved rigid members 30 and 30' are rigidly mounted. The curvature of members 30 and 30' is such that substantially follows the contour of the space between vertebrae. Obviously, the radius of curvature of members 30 and 30' will be different for cervical vertebrae than for lumbar vertebrae. It is important to note that when wires 50 are tightened, distraction is produced in the spine section primarily by forcing the end vertebrae of the section axially outwardly thereby correcting the deformity. Also, when the wires 50 are tightened, there is a certain amount of de-rotation (rotation back to normal) accomplished on the vertebrae in the middle, if needed, and the spine is reduced to the middle line.

Hook members 40 and 40' are disposed outwardly on members 30 and 30' while hook members 42 and 42' are outwardly disposed substantially towards the ends of elongated members 20 and 20'. Hook members 40; 40'; 42 and 42' have a substantially triangular or wedge shape and cooperate with each other to provide a firm anchorage point for wire 50 that is used to tie device 10 to the vertebrae at both ends of device 10. Preferably, the hook members are either casted or soldered to members 20; 20'; 30 and 30' on their periphery.

Device 10, when properly implanted, corrects and stabilizes permanently spinal deformities. Members 20; 20'; 30; 30'; 40; 40'; 42 and 42' are made out of stainless steel, preferably. For scoliosis patients, parallel members 20 and 20' are substantially straight. For kyphosis and lordosis patients, parallel members 20 and 20' are curved as needed to bring the necessary correction to the spine.

It is believed the foregoing description conveys the best understanding of the objects and advantages of the present invention. Different embodiments may be made of the inventive concept of this invention. It is to be understood that all matter disclosed herein is to be interpreted merely as illustrative, and not in a limiting sense.

What is claimed is:

1. A device for stabilizing and correcting deformations of the spine being surgically mountable over the vertebrae, comprising:
    A. two elongated rigid members parallel to each other and each member having two ends;
    B. two curved rigid members rigidly mounted on the respective ends of said elongated members so that said elongated members are kept in a space apart relationship from each other and the four members form a rigid rectangular frame;
    C. a plurality of integrally built in hook members having a wedge shape outwardly mounted on the outer periphery of said curved and elongated members; and
    D. wire means for tying said device to the vertebrae of said spine by using said hook members as anchorage points.

2. The device set forth in claim 1 wherein said elongated and curved members and said hook members are made out of stainless steel.

3. The device set forth in claim 2 wherein said hook members are mounted on said curved members and on said elongated members substantially towards their respective ends of said elongated members so that they cooperate among themselves to provide a firm anchorage point to said wire means.

4. The device set forth in claim 3 including two of said hook members mounted on each of said curved members and two of said hook members mounted substantially toward the ends of said elongated members so that said wire means may be inserted around the vertebrae adjacent to said ends thereby said members cooperatively provide a firm anchorage point for said wire means.

5. The device set forth in claim 4 wherein the radius of curvature of said curved members follows the contour of said vertebrae.

* * * * *